US012766280B2

(12) United States Patent
Dong et al.

(10) Patent No.: US 12,766,280 B2
(45) Date of Patent: Oct. 20, 2026

(54) BREATHING DEVICE WITH CARBON DIOXIDE COMPENSATION FUNCTION

(71) Applicant: GUANGZHOU LANSWICK MEDICAL TECHNOLOGY CO., LTD., Guangzhou (CN)

(72) Inventors: Hui Dong, Guangzhou (CN); Longchao Zhao, Guangzhou (CN); Caixin Sun, Guangzhou (CN)

( * ) Notice: Subject to any disclaimer, the term of this patent is extended or adjusted under 35 U.S.C. 154(b) by 826 days.

(21) Appl. No.: 18/031,572

(22) PCT Filed: Nov. 4, 2022

(86) PCT No.: PCT/CN2022/129965
§ 371 (c)(1),
(2) Date: Apr. 12, 2023

(87) PCT Pub. No.: WO2023/207023
PCT Pub. Date: Nov. 2, 2023

(65) Prior Publication Data

US 2024/0366890 A1 Nov. 7, 2024

(30) Foreign Application Priority Data

Apr. 26, 2022 (CN) ........................ 202210450492.9

(51) Int. Cl.
*A61M 16/00* (2006.01)
*A61M 16/10* (2006.01)
(Continued)

(52) U.S. Cl.
CPC .... *A61M 16/0045* (2013.01); *A61M 16/0051* (2013.01); *A61M 16/026* (2017.08);
(Continued)

(58) Field of Classification Search
CPC .......... A61M 16/0045; A61M 16/0051; A61M 16/105; A61M 16/12; A61M 16/16;
(Continued)

(56) References Cited

U.S. PATENT DOCUMENTS 3,593,710 A * 7/1971 Eichelman ............ A61M 16/18 128/200.11
5,237,987 A * 8/1993 Anderson ............ A61M 16/12 128/204.21
(Continued)

FOREIGN PATENT DOCUMENTS

CA 2849155 A1 * 11/2014 ............ A61M 16/00
CN 109498928 A * 3/2019 ............ A61M 11/02
(Continued)

OTHER PUBLICATIONS

English translation for CA 2849155, machine translated by espacenet.com.*
(Continued)

*Primary Examiner* — Tu A Vo

(57) ABSTRACT

A breathing device with carbon dioxide compensation function includes an air source pipeline, a low pressure oxygen source pipeline, a high pressure oxygen source pipeline, a carbon dioxide source pipeline, a gas supply pipeline all of which are set in a ventilator and corresponding to an air source, a lower pressure oxygen source, a high pressure oxygen source and a carbon dioxide source respectively; and a breathing pipeline which is set outside the ventilator. The breathing device further includes a carbon dioxide flow regulation system for detecting and regulating carbon dioxide in the breathing gas which is transported by the breathing device for patients.

7 Claims, 3 Drawing Sheets

(51) Int. Cl.
*A61M 16/12* (2006.01)
*A61M 16/16* (2006.01)
*A61M 16/20* (2006.01)

(52) U.S. Cl.
CPC .......... *A61M 16/105* (2013.01); *A61M 16/12* (2013.01); *A61M 16/16* (2013.01); *A61M 16/208* (2013.01); *A61M 16/0003* (2014.02); *A61M 2016/0027* (2013.01); *A61M 2016/003* (2013.01); *A61M 2016/1025* (2013.01); *A61M 2016/103* (2013.01); *A61M 2202/0208* (2013.01); *A61M 2202/0225* (2013.01); *A61M 2205/18* (2013.01); *A61M 2205/3334* (2013.01); *A61M 2205/3355* (2013.01); *A61M 2230/005* (2013.01); *A61M 2230/04* (2013.01); *A61M 2230/30* (2013.01); *A61M 2230/42* (2013.01)

(58) Field of Classification Search
CPC ........ A61M 16/208; A61M 2202/0208; A61M 2202/0225; A61M 2205/18; A61M 2205/3334; A61M 2205/3355; A61M 16/026; A61M 2016/0027; A61M 2016/003; A61M 2016/1025; A61M 2016/103; A61M 2230/005; A61M 2230/04; A61M 2230/30; A61M 2230/42; A61M 16/0003; A61M 16/10; A61M 16/1005; A61M 11/02
See application file for complete search history.

(56) References Cited

U.S. PATENT DOCUMENTS 6,378,520 B1 * 4/2002 Davenport ............ A61M 16/20 128/205.24
2002/0185126 A1 * 12/2002 Krebs ................. A61M 16/202 128/200.24
2007/0049841 A1 * 3/2007 Lepel .................... A61M 16/06 600/534
2007/0062532 A1 * 3/2007 Choncholas ........ A61M 16/024 128/204.23
2013/0239968 A1 * 9/2013 Friberg ............. A61M 16/0066 128/204.23
2014/0144434 A1 * 5/2014 Martin ................ A61M 16/104 128/203.14
2016/0287824 A1 * 10/2016 Chang ................. A61M 16/204
2016/0346498 A1 * 12/2016 Tector ................ A61B 5/14551
2017/0361043 A1 * 12/2017 Krüger .............. A61M 16/0051
2019/0321576 A1 * 10/2019 Boulanger ............ A61M 16/12
2020/0345914 A1 * 11/2020 Turner .................... A61M 1/14
2020/0368464 A1 * 11/2020 Brunetto Tancredi ....................... A61B 5/087
2021/0052844 A1 * 2/2021 Oldfield ............... A61B 5/7246
2022/0241528 A1 * 8/2022 McCormick ........ A61M 16/022

FOREIGN PATENT DOCUMENTS

CN 113413529 A * 9/2021 ........ A61M 16/0003
CN 113967222 A * 1/2022 ............ A61M 16/12
FR 2977163 A1 * 1/2013 ........ A61M 16/1015
FR 3098727 A1 * 1/2021 ........ A61M 16/0051
JP H0984876 A * 3/1997
WO WO-2016001448 A1 * 1/2016 .......... A61M 16/209
WO WO-2018137780 A1 * 8/2018 ............. A61B 5/082

OTHER PUBLICATIONS

English translation for CN 109498928, machine translated by espacenet.com.*
English translation for CN 113413529, machine translated by espacenet.com.*
English translation for CN 113967222, machine translated by espacenet.com.*
English translation for JPH 0984876, machine translated by espacenet.com.*

* cited by examiner

BREATHING DEVICE WITH CARBON DIOXIDE COMPENSATION FUNCTION

BACKGROUND OF THE PRESENT INVENTION

Field of Invention

The present invention relates to the technical field of breathing device, and more particularly to a breathing device with carbon dioxide compensation function.

Description of Related Arts

According to the service environment, ventilators are divided into medical ventilators and household ventilators. Medical ventilators are used under the supervision of medical staff for patients with respiratory failure and barotrauma, as well as those requiring respiratory support, respiratory treatment, and first aid resuscitation. The medical ventilators mainly include therapeutic ventilators, first aid ventilators, out-of-hospital transport ventilators, high-frequency jet ventilators, high-frequency oscillation ventilators. Household ventilators are used to relieve snoring, hypopnea and sleep apnea during sleep, moderate and mild respiratory failure, and respiratory insufficiency, thus achieving adjuvant therapeutic purposes. They are commonly used in the family environment, and is also able to be used in medical institutions, and mainly include household respiratory support equipment, sleep ventilators, sleep non-invasive ventilators, continuous positive pressure ventilators, bilevel positive airway pressure ventilators and positive pressure ventilation therapy apparatuses.

Currently, the air source of all ventilators is air and pure oxygen. Existing ventilators are only able to provide patients with mixed air-oxygen, air or pure oxygen, and are unable to provide patients with carbon dioxide gas. Therefore, existing ventilators are unable to compensate for carbon dioxide in the body of the patient by adjusting the proportion of carbon dioxide in the supplied air.

SUMMARY OF THE PRESENT INVENTION

The present invention provides a breathing device with carbon dioxide compensation function, so as to solve the above problems in the prior art.

A breathing device with carbon dioxide compensation function comprises:

an air source pipeline, a low pressure oxygen source pipeline, a high pressure oxygen source pipeline, a carbon dioxide source pipeline, a gas supply pipeline all of which are set in a ventilator; and a breathing pipeline which is set outside the ventilator, wherein:

air from an air source enters the ventilator through the air source pipeline, low pressure oxygen from a low pressure oxygen source is mixed with the air in the air source pipeline through the low pressure oxygen source pipeline; mixed breathing gas enters the gas supply pipeline, is transmitted outside the ventilator through the gas supply pipeline, and is inhaled by a user through the breathing pipeline;

high pressure oxygen from a high pressure oxygen source enters the ventilator through the high pressure oxygen source pipeline, carbon dioxide gas from a carbon dioxide source and the high pressure oxygen in the high pressure oxygen source pipeline are mixed through the carbon dioxide source pipeline and form therapeutic gas; the therapeutic gas enters the gas supply pipeline, is transmitted outside the ventilator through the gas supply pipeline, and is inhaled by the user through the breathing pipeline for treatment, wherein the carbon dioxide gas is mixed with the high pressure oxygen in a preset ratio.

Preferably, a first filter is provided on the air source pipeline, a second filter and a first check valve are provided on the low pressure oxygen source pipeline, the low pressure oxygen flows through the second filer and first check valve in sequence and enters an oxygen flow sensor, the low pressure oxygen and the air from the oxygen flow sensor enter a breathing gas generator through a second check valve, and are mixed by the breathing gas generator for forming breathing gas;

a first pressure sensor is provided on the low pressure oxygen source pipeline and is located between the first check valve and the oxygen flow sensor for measuring a pressure of the low pressure oxygen in the low pressure oxygen source pipeline, the breathing gas enters the gas supply pipeline through a third check valve.

Preferably, a third filter, a first flow control valve, and a directional valve are provided on the high pressure oxygen source pipeline, a second pressure sensor is located between the third filter and the first flow control valve; when the directional valve is opened positively, the high pressure oxygen enters the gas supply pipeline through the third filter, the first flow control valve, and the directional valve on the high pressure oxygen source pipeline;

a fourth filter, a third pressure sensor and a second flow control valve are provided on the carbon dioxide source pipeline in sequence, the carbon dioxide gas and the high pressure oxygen are mixed through the fourth filter, the third pressure sensor and the second flow control valve on the carbon dioxide source pipeline and form therapeutic gas, the therapeutic gas enters the gas supply pipeline;

the third pressure sensor measures a pressure of the carbon dioxide gas in the carbon dioxide source pipeline; a ratio of oxygen to the carbon dioxide gas in the therapeutic gas is adjusted through adjusting a flow of the high pressure oxygen and the carbon dioxide gas by the first and second flow control valves, so as to allow the ratio reaches a preset value.

Preferably, an oxygen sensor, a carbon dioxide sensor, a fourth pressure sensor and a gas flow sensor are provided on the gas supply pipeline;

the oxygen sensor detects an oxygen concentration in the gas supply pipeline, the carbon dioxide sensor detects a carbon dioxide concentration in the gas supply pipeline, the fourth pressure sensor detects a gas concentration in the gas supply pipeline, and the gas flow sensor detects a gas flow in the gas supply pipeline.

Preferably, a humidifier and a nebulizer are provided on a breathing pipeline, a fifth pressure sensor is located between the humidifier and the nebulizer, the breathing gas or the therapeutic gas enters a body of the user through the nebulizer;

atomizing gas of the nebulizer is from the high pressure oxygen in the high pressure oxygen source pipeline, the high pressure oxygen enters an atomizing pipeline through a shut-off valve, and then enters the nebulizer through a first throttle valve for atomizing medication.

Preferably, the breathing gas or the therapeutic gas enters the body of the user through the nebulizer, which specifically comprises:

the breathing gas or the therapeutic gas enters the body of the user through the nebulizer via a mask or a respiratory tube;

when the user exhales gas through the mask or the respiratory tube, the exhaled gas enters an expiratory pipeline, the expiratory pipeline is provided with a diaphragm regulating valve, and the exhaled gas enters an external environment through the diaphragm regulating valve;

the high pressure oxygen source pipeline is connected with a PEEP (positive end-expiratory pressure) regulating pipeline, the PEEP regulating pipeline is provided with a pressure regulating valve, a sixth pressure sensor and a second throttle valve; the sixth pressure sensor is connected with the diaphragm regulating valve for detecting PEEP; a pressure of the diaphragm regulating valve is adjusted by the sixth pressure sensor and the second throttle valve;

the pressure regulating valve is opened to a position according to a preset PEEP value, and diverted high pressure oxygen in the high pressure source pipeline enters the external environment through the second throttle valve.

Preferably, the fifth pressure sensor is connected with an alarm; when the fifth pressure sensor detects that a pressure exceeds a preset range, an alarm instruction is sent to the alarm, and the alarm sends out an abnormal pressure alarm to remind occurrence of gas path blockage or gas leakage.

Preferably, when the directional valve is opened reversely, the high pressure oxygen in the high pressure oxygen source pipeline will not enter the gas supply pipeline.

Preferably, the breathing device further comprises an auxiliary gas source pipeline, the auxiliary gas source pipeline is provided with a fifth filter and the a flow control valve, and a seventh pressure sensor is located between the fifth filter and the third flow control valve;

auxiliary gas from an auxiliary gas source is mixed with the high pressure oxygen and the carbon dioxide gas through the auxiliary gas source pipeline, and mixed gas enters the gas supply pipeline;

the auxiliary gas from the auxiliary gas source comprises carbon dioxide and medical gas used by a medical industry for inhalation by the user.

Preferably, the breathing device further comprises a carbon dioxide flow regulation system which comprises a carbon dioxide monitoring AI (artificial intelligence) module;

the carbon dioxide monitoring AI module detects physiological information of the user in real time, wherein the physiological information comprises blood pressure, ECG (electrocardiogram) parameters, $FiO_2$ (fraction of inspiration oxygen), $FiCO_2$ (fraction of inspiration carbon dioxide), respiratory rate, and respiratory tidal volume; the carbon dioxide monitoring AI module predicts the respiratory state of the user on the physiological information based on comprehensive data analysis AI algorithm, determines a ratio of the carbon dioxide and the oxygen according to the respiratory state, and sets the determined ratio of the carbon dioxide and the oxygen to a preset ratio;

the carbon dioxide flow regulation system further comprises a prediction module, wherein the prediction module, which is connected with the carbon dioxide monitoring AI module for obtaining the physiological information, is configured to determine a first time from starting the ventilator to the user inhaling the therapeutic gas, and a second time from the user inhaling the therapeutic gas into the carbon dioxide monitoring AI module for detection to recovery of the physiological information of the user;

based on the first time, the second time, and the physiological information of the user, a pre-opening time is determined, one pre-opening time is corresponding to one opening condition, wherein the opening condition is when the carbon dioxide gas in the body of the user or exhaled by the user exceeds the preset range, the ventilator is started.

Compared with the prior art, the present invention has some advantages as follows.

The present invention provides the breathing device with carbon dioxide compensation function. The breathing device comprises an air source pipeline, a low pressure oxygen source pipeline, a high pressure oxygen source pipeline, a carbon dioxide source pipeline, a gas supply pipeline all of which are set in a ventilator; and a breathing pipeline which is set outside the ventilator. The air from an air source enters the ventilator through the air source pipeline. The low pressure oxygen from a low pressure oxygen source is mixed with the air in the air source pipeline through the low pressure oxygen source pipeline; mixed breathing gas enters the gas supply pipeline, is transmitted outside the ventilator through the gas supply pipeline, and is inhaled by a user through the breathing pipeline. The high pressure oxygen from a high pressure oxygen source enters the ventilator through the high pressure oxygen source pipeline, carbon dioxide gas from a carbon dioxide source and the high pressure oxygen in the high pressure oxygen source pipeline are mixed through the carbon dioxide source pipeline and form therapeutic gas. the therapeutic gas enters the gas supply pipeline, is transmitted outside the ventilator through the gas supply pipeline, and is inhaled by the user through the breathing pipeline for treatment, wherein the carbon dioxide gas is mixed with the high pressure oxygen in a preset ratio. Moreover, the breathing device further comprises the carbon dioxide flow regulation system for detecting and regulating carbon dioxide in the breathing gas which is transported by the breathing device for patients, so as to compensate for the carbon dioxide in the body of the patient. The carbon dioxide flow control parameters are dynamically adjusted for preventing patients from hyperventilation, and there is no need to collect the carbon dioxide gas exhaled or produced by patients in this process.

Other features and advantages of the present invention will be described in the subsequent specification, and partially become apparent from the specification, or be understood by implement the present invention. Objects and other advantages of the present invention are able to be realized and obtained by the structure specified in the specification, claims, and drawings.

The technical solutions of the present invention are further described in detail by the accompanying drawings and embodiments as follows.

BRIEF DESCRIPTION OF THE DRAWINGS

The present invention is able to be further understood with accompanying drawings. The drawings are a part of the specification and are used to explain the present invention in combination with embodiments as follows, which are not a limitation of the present invention.

Figure 1:
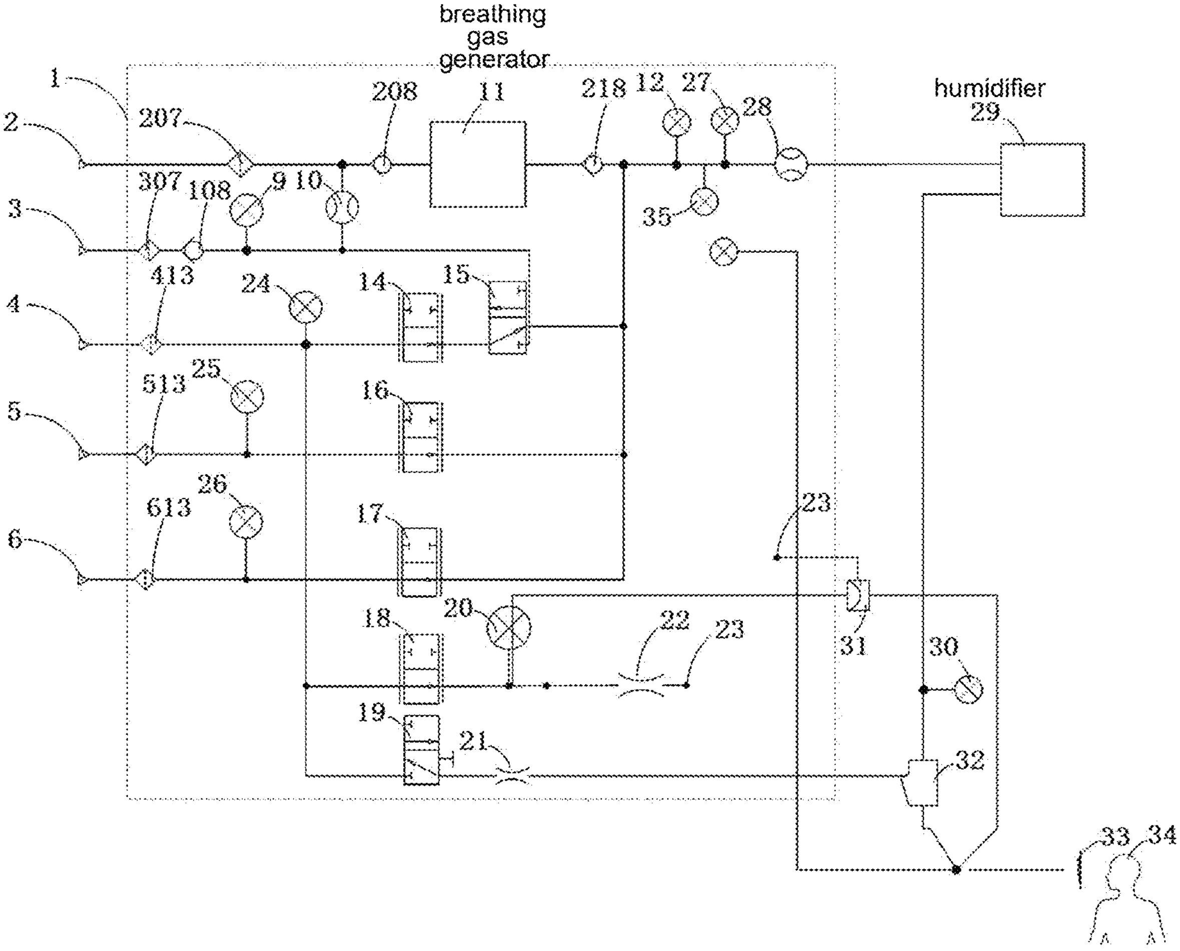
FIG. 1 is a structural schematic diagram of a breathing device with carbon dioxide compensation function provided by the present invention.

In the drawings, 1: ventilator; 2: air source; 3: low pressure oxygen source; 4: high pressure oxygen source; 5: carbon dioxide source; 6: auxiliary gas source; 9: first pressure sensor; 10: oxygen flow sensor; 11: breathing gas generator; 12: carbon oxide sensor; 14: first flow control valve; 15: directional valve; 16: second flow control valve; 17: third flow control valve; 18: pressure regulating valve; 19: shut-off valve; 20: sixth pressure sensor; 21: first throttle valve; 22: second throttle valve; 23: external environment; 24: second pressure sensor; 25: third pressure sensor; 26: seventh pressure sensor; 27: oxygen sensor; 28: gas flow sensor; 29: humidifier; 30: fifth pressure sensor; 31: diaphragm regulating valve; 32: nebulizer; 33: mask; 34: user; 35: fourth pressure sensor; 36: carbon dioxide flow regulation system; 38: physiological detection instrument; 40: carbon dioxide monitoring AI (artificial intelligence) module; 108: first check valve; 207: first filter; 208: second check valve; 218: third check valve; 307: second filter; 413: third filter; 513: fourth filter; 613: fifth filter.

DETAILED DESCRIPTION OF THE PREFERRED EMBODIMENT

The present invention will be further described in detail with reference to the accompanying drawings and embodiments. It should be understood that the preferred embodiments described herein are intended only to illustrate and explain the present invention and are not intended to limit the present invention.

Figure 2:
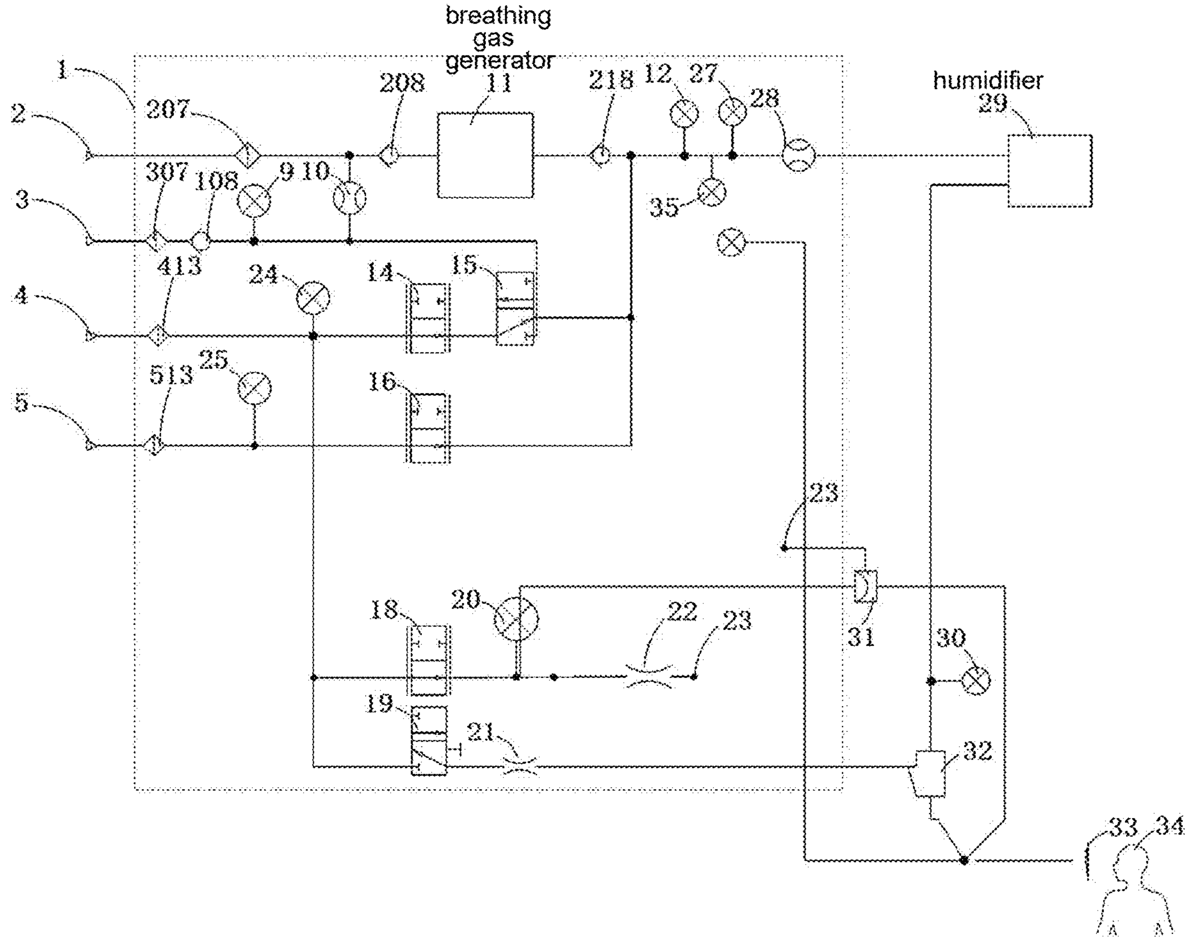
FIG. 2 is another structural schematic diagram of the breathing device with carbon dioxide compensation function provided by the present invention.
Figure 3:
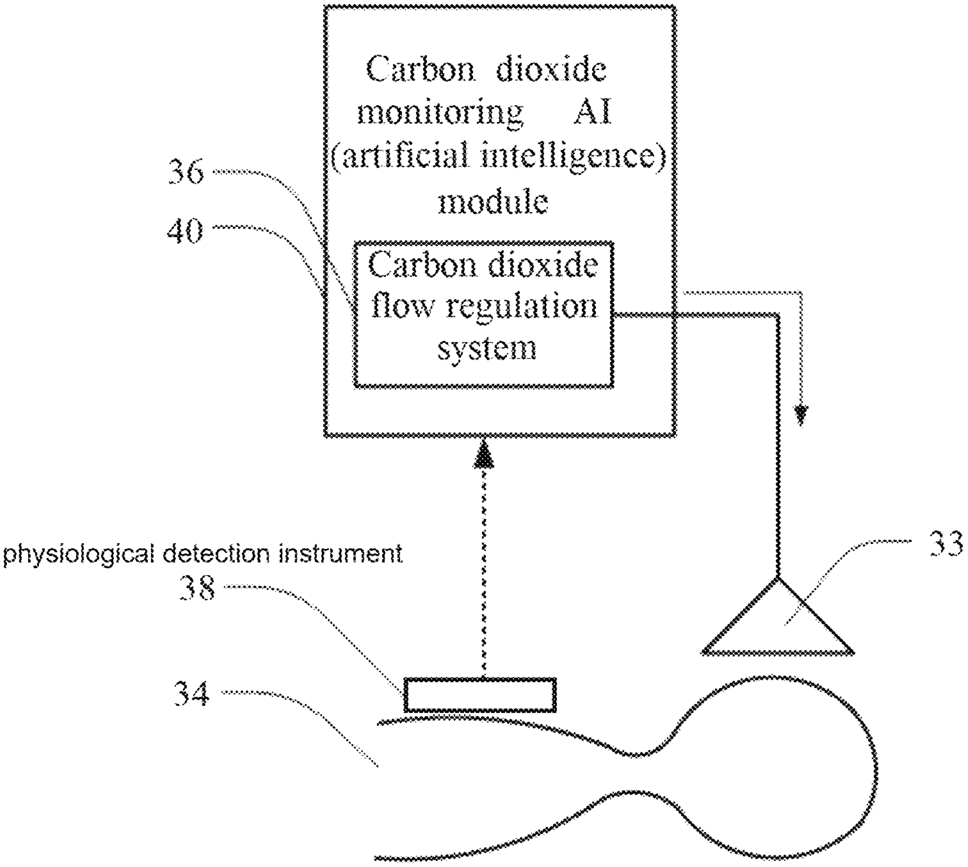
FIG. 3 is a structural schematic diagram of a carbon dioxide flow regulation system.

Referring to FIGS. 1 and 2, a breathing device with carbon dioxide compensation function is illustrated. The breathing device comprises an air source pipeline, a low pressure oxygen source pipeline, a high pressure oxygen source pipeline, a carbon dioxide source pipeline, a gas supply pipeline all of which are set in a ventilator 1; and a breathing pipeline which is set outside the ventilator 1, wherein:

the air from the air source 2 enters the ventilator 1 through the air source pipeline, the low pressure oxygen from the low pressure oxygen source 3 is mixed with the air in the air source pipeline through the low pressure oxygen source pipeline; the mixed breathing gas enters the gas supply pipeline, is transmitted outside the ventilator 1 through the gas supply pipeline, and is inhaled by a user 34 through the breathing pipeline;

the high pressure oxygen from the high pressure oxygen source 4 enters the ventilator 1 through the high pressure oxygen source pipeline, the carbon dioxide gas from the carbon dioxide source 5 and the high pressure oxygen in the high pressure oxygen source pipeline are mixed through the carbon dioxide source pipeline and form the therapeutic gas; the therapeutic gas enters the gas supply pipeline, is transmitted outside the ventilator 1 through the gas supply pipeline, and is inhaled by the user 34 through the breathing pipeline for treatment, wherein the carbon dioxide gas is mixed with the high pressure oxygen in a preset ratio.

The working principle of the above technical solution is as follows. According to the present invention, there are two breathing control systems in the breathing device, namely, a therapeutic breathing system and an universal breathing system, wherein the two breathing control systems share the same gas supply pipeline; in the therapeutic breathing system, the high pressure oxygen from the high pressure oxygen source 4 and the carbon dioxide gas from the carbon dioxide source 5 are mixed to form the therapeutic gas for the user 34; in the universal breathing system, the low pressure oxygen from the low pressure oxygen source 3 and the air from the air source 2 are mixed to form the breathing gas for the user 34.

Specifically, the breathing device comprises an air source 2, a low pressure oxygen source 3, a high pressure oxygen source 4, a carbon dioxide source 5, a first pressure sensor 9, an oxygen flow sensor 10, a first flow control valve 14, a directional valve 15, a shut-off valve 19, a sixth pressure sensor 20, a first throttle valve 21, a second throttle valve 22, a fifth pressure sensor 30, a diaphragm regulating valve 31, a nebulizer 32, a first check valve 108, a first filter 207, a second filter 307, a third filter 413, a fourth filter 513 and a fifth filter 613.

When the general breathing function is activated, the directional valve 15 is switched and connected with the oxygen flow sensor 10, the high pressure oxygen from the high pressure oxygen source 4 flows through the third filter 413 for entering the ventilator 1, a proportion of the oxygen in the respiratory airflow for the user 34 is set through the first flow control valve 14, the second pressure sensor 24 monitors the pressure of the high pressure oxygen entering the ventilator 1, and the oxygen sensor 27 detects the oxygen concentration. When no high pressure oxygen source 4 is provided, the low pressure oxygen source 3 is provided, the low pressure oxygen from the low pressure oxygen source flows through the first check valve 108 and enters the oxygen flow sensor 10, the first pressure sensor 9 monitors the pressure of the low pressure oxygen, the flow of the low pressure oxygen is determined by the low pressure oxygen source 3 and is generally not higher than 15 L/min. The air from the air source 2 flows through the first filter 207 for entering the ventilator 1, and then is mixed with the oxygen from the oxygen flow sensor 10, and then enters the breathing gas generator 11 through the second check valve 208. The tidal gas generated by the breathing gas generator 11 flows through the third check valve 218 and enters the gas supply pipeline. The oxygen sensor 27 detects the oxygen concentration. The gas flow sensor 28 detects the flow of the tidal gas. The fourth pressure sensor 35 detects the pressure of the gas supply pipeline. The tidal gas flows outside the ventilator 1 and enters the respiratory tube of the user. If the humidity and temperature of the tidal gas need to be adjusted, the humidifier 29 is able to be connected with the ventilator 1 in series. If medication needs to be added to the tidal gas, the breathing pipeline is provided with a nebulizer 32, and at this time, the shut-off valve 19 is switched on, the diverted gas from the high pressure oxygen source 4 flows through the first throttle valve 21 and enters the nebulizer 32 for nebulizing the medication; the tidal gas is inhaled by the user 34 through a mask 33 or the respiratory pipeline. The exhaled gas from the user flows through the diaphragm regulating valve 31 and enters the external environment 23. The pressure of the diaphragm regulating valve 31 is adjusted by the sixth pressure sensor 20 and the second throttle valve 22. While using the PEEP (positive end-expiratory pressure) regulating function, the pressure regulating valve 18 is opened to a certain position according to the preset value of PEEP, the diverted gas from the high pressure oxygen source 4 flows through the second throttle valve 22 and enters the external environment 23; the sixth pressure sensor 20 is connected with the pressure regulating valve 18 and the second throttle valve 22, so the sixth pressure sensor 20 monitors the pressure between the pressure regulating valve 18 and the second throttle valve 22. The sixth pressure sensor 20 is also connected with the diaphragm regulating valve 31, so the pressure of the location where the pressure regulating valve 18, the sixth pressure sensor 20, the second throttle valve 22 and the diaphragm regulating valve 31 are connected is defined as PEEP.

Beneficial effects of the above technical solution are as follows. There is a carbon dioxide flow regulation system 36 in the ventilator 1 for detecting and regulating the carbon dioxide gas in the breathing gas which is delivered to the user by the ventilator 1, so as to compensate for the amount of carbon dioxide or hydrogen ions $H^+$ in the user's body, so that the flow control parameters of the carbon dioxide gas are dynamically adjusted for preventing the user from hyperventilation, and there is no need to collect the carbon dioxide gas exhaled or produced by the user in this process.

Preferably, the first filter 207 is provided on the air source pipeline, that is, the first filter 207 is connected with the air source 2; the second filter 307 and the first check valve 108 are provided on the low pressure oxygen source pipeline, that is, the second filter 307 is located between the low pressure oxygen source 3 and the first check valve 108; the low pressure oxygen flows through the second filer 307 and first check valve 108 in sequence and enters the oxygen flow sensor 10, the low pressure oxygen and the air from the oxygen flow sensor 10 enter the breathing gas generator 11 through the second check valve 208, and are mixed by the breathing gas generator 11 for forming the breathing gas;

the first pressure sensor 9 is provided on the low pressure oxygen source pipeline and is located between the first check valve 108 and the oxygen flow sensor 10 for measuring the pressure of the low pressure oxygen in the low pressure oxygen source pipeline, the breathing gas enters the gas supply pipeline through the third check valve 218.

Preferably, the third filter 413, the first flow control valve 14, and the directional valve 15 are provided on the high pressure oxygen source pipeline, the second pressure sensor 24 is located between the third filter 413 and the first flow control valve 14; when the directional valve 15 is opened positively, the high pressure oxygen enters the gas supply pipeline through the third filter 413, the first flow control valve 14, and the directional valve 15 on the high pressure oxygen source pipeline;

the fourth filter 513, the third pressure sensor 25 and the second flow control valve 16 are provided on the carbon dioxide source pipeline in sequence, the carbon dioxide gas and the high pressure oxygen are mixed through the fourth filter 513, the third pressure sensor 25 and the second flow control valve 16 on the carbon dioxide source pipeline and form the therapeutic gas, the therapeutic gas enters the gas supply pipeline;

the third pressure sensor 25 measures the pressure of the carbon dioxide gas in the carbon dioxide source pipeline; the ratio of the oxygen to the carbon dioxide gas in the therapeutic gas is adjusted through adjusting the flow of the high pressure oxygen and the carbon dioxide gas by the first and second flow control valves 14, 16, so as to allow the ratio reaches reach the preset value.

Preferably, the oxygen sensor 27, the carbon dioxide sensor 12, the fourth pressure sensor 35 and the gas flow sensor 28 are provided on the gas supply pipeline;

the oxygen sensor 27 detects the oxygen concentration in the gas supply pipeline, the carbon dioxide sensor 12 detects the carbon dioxide concentration in the gas supply pipeline, the fourth pressure sensor 35 detects the gas concentration in the gas supply pipeline, and the gas flow sensor 28 detects the gas flow in the gas supply pipeline.

Preferably, the humidifier 29 and the nebulizer 32 are provided on the breathing pipeline, the fifth pressure sensor 30 is located between the humidifier 29 and the nebulizer 32, the breathing gas or the therapeutic gas enters the body of the user 34 through the nebulizer 32;

the atomizing gas of the nebulizer 32 is from the high pressure oxygen in the high pressure oxygen source pipeline, and the high pressure oxygen enters the atomizing pipeline through the shut-off valve 19.

Preferably, the breathing gas or the therapeutic gas enters the body of the user 34 through the nebulizer 32, which specifically comprises:

the breathing gas or the therapeutic gas enters the body of the user 34 through the nebulizer 32 via the mask 33 or the respiratory tube;

when the user 34 exhales gas through the mask 33 or the respiratory tube, the exhaled gas enters the expiratory pipeline, the expiratory pipeline is provided with the diaphragm regulating valve 31, and the exhaled gas enters the external environment 23 through the diaphragm regulating valve 31;

the high pressure oxygen source pipeline is connected with the PEEP regulating pipeline, the PEEP regulating pipeline is provided with the pressure regulating valve 18, the sixth pressure sensor 20 and the second throttle valve 22; the sixth pressure sensor 20 is connected with the diaphragm regulating valve 31 for detecting the PEEP; the pressure of the diaphragm regulating valve 31 is adjusted by the sixth pressure sensor 20 and the second throttle valve 22;

the pressure regulating valve 18 is opened to a position according to the preset PEEP value, and the diverted high pressure oxygen in the high pressure source pipeline enters the external environment through the second throttle valve.

PEEP is the positive end-expiratory pressure for reinflating collapsed alveoli, increasing mean airway pressure, improving oxygenation, and reducing pulmonary edema, but at the same time affecting cardiac blood return and left ventricular afterload, and overcoming increased respiratory work. PEEP is often applied to I-type respiratory failure represented by ARDS (Acute Respiratory Distress Syndrome).

Preferably, the fifth pressure sensor 30 is connected with an alarm; when the fifth pressure sensor 30 detects that the pressure exceeds the preset range, an alarm instruction is sent to the alarm, and the alarm sends out an abnormal pressure alarm to remind the occurrence of gas path blockage or gas leakage.

Preferably, when the directional valve 15 is opened reversely, the high pressure oxygen in the high pressure oxygen source pipeline will not enter the gas supply pipeline.

Preferably, the breathing device further comprises an auxiliary gas source pipeline, the auxiliary gas source pipeline is provided with the fifth filter 613 and the third flow control valve 17, and the seventh pressure sensor 26 is located between the fifth filter 613 and the third flow control valve 17;

the auxiliary gas from the auxiliary gas source 6 is mixed with the high pressure oxygen and the carbon dioxide gas through the auxiliary gas source pipeline, and the mixed gas enters the gas supply pipeline;

the auxiliary gas from the auxiliary gas source 6 comprises the carbon dioxide gas and the medical gas used by the medical industry for inhalation by the user 34.

Preferably, the breathing device further comprises the carbon dioxide flow regulation system 36 which comprises a carbon dioxide monitoring AI (artificial intelligence) module 40;

the carbon dioxide monitoring AI module 40 detects the physiological information of the user 34 in real time, wherein the physiological information comprises blood pressure, ECG (electrocardiogram) parameters, $FiO_2$ (fraction of inspiration oxygen), $FiCO_2$ (fraction of inspiration carbon dioxide), respiratory rate, and respiratory tidal volume; the carbon dioxide monitoring AI module 40 predicts the respiratory state of the user 34 on the physiological information based on the comprehensive data analysis AI algorithm, determines the ratio of the carbon dioxide and the oxygen according to the respiratory state, and sets the determined ratio of the carbon dioxide and the oxygen to a preset ratio;

the carbon dioxide flow regulation system 36 further comprises a prediction module, wherein the prediction module, which is connected with the carbon dioxide monitoring AI module 40 for obtaining the physiological information, is configured to determine the first time from starting the ventilator 1 to the user 34 inhaling the therapeutic gas, and the second time from the user 34 inhaling the therapeutic gas into the carbon dioxide monitoring AI module 40 for detection to the recovery of the physiological information of the user 34;

based on the first time, the second time, and the physiological information of the user 34, the pre-opening time is determined, one pre-opening time is corresponding to one opening condition, wherein the opening condition is when the carbon dioxide gas in the body of the user 34 or exhaled by the user 34 exceeds the preset range, the ventilator 1 is started.

The working principle of the above technical solution is as follows. The carbon dioxide flow regulation system comprises a high pressure oxygen source 4, a carbon dioxide source 5, a third filter 413, a fourth filter 513, a first pressure sensor 24, a second pressure sensor 25, a first flow control valve 14, a second flow control valve 16, and a fifth pressure sensor 30 which is a pressure sensor close to the user. When the carbon dioxide regulation function is activated, the carbon dioxide gas from the carbon dioxide source 5 flows through the fourth filter 513 and enters the ventilator 1; by adjusting the second flow control valve 16, the flow of the carbon dioxide in the breathing gas for the patient or the user 34 is set. The carbon dioxide sensor 12 detects the concentration of the carbon dioxide gas from the carbon dioxide source 5.

FIG. 2 shows the carbon dioxide monitoring AI module 40 based on the carbon dioxide flow regulation system. The carbon dioxide monitoring AI module 40 drives the carbon dioxide flow regulation system 36 to work, so as to provide required carbon dioxide gas for entering the pipeline located at a rear end of the third check valve 218, and then the carbon dioxide is mixed with other gases and sent to the patient or the user 34 through the mask 33. Herein, the required carbon dioxide gas meets the set parameters which are $PCO_2$ (partial pressure of carbon dioxide), $FiCO_2$ and flow of carbon dioxide. The carbon dioxide monitoring AI module 40 obtains the physiological information (including blood pressure, ECG parameters, $FiO_2$, $FiCO_2$, respiratory rate, and respiratory tidal volume) of the patient through the physiological detection instrument 38 in real time, predicts the respiratory state of the patient on the physiological information based on the comprehensive data analysis AI algorithm, determines the possibility of hyperventilation, respiratory alkalosis, respiratory acidosis, hypoxidosis and other diseases, and according to the determination results, $CO_2$ parameters are dynamically adjusted independently to prevent patients from developing the above symptoms.

When the general respiratory function is activated, the tidal volume VT, the respiratory time ratio I:E, the oxygen ratio $FiO_2$, and the PEEP are set; the appropriate breathing mode is selected according to the state of the patient, and then the ventilator 1 starts to work.

When the therapeutic function is started, the tidal volume VT, the respiratory time ratio I:E, the oxygen ratio $FiO_2$, and the PEEP are set, and then the ventilator 1 starts to work. If the pressure is abnormal at the fifth pressure sensor 30, it indicates the gas path blockage or gas leakage. Medical personnel need to check the state of gas path. The therapeutic gas is a mixture of oxygen and carbon dioxide. The two gases are mixed in a fixed proportion and then injected into the poisoned patient for treatment. Other medical gases are also able to be mixed according to the above method and then injected into patients through continuous ventilation or other customized ventilation modes.

The beneficial effects of the above technical solution are as follows. The $CO_2$ monitoring AI module 40 is able to automatically adjust $FiCO_2$ according to the physiological condition of the patient, which prevents the patient from hyperventilation while regulating $CO_2$. In addition, the pre-opening time is preset, the first time and the second time are calculated, the ratio of carbon dioxide to oxygen is adjusted in advance according to the change rule and trend of carbon dioxide content in the body of the user 34, or the therapeutic function of the ventilator 1 is activated in advance to timely supplement the carbon dioxide gas or reduce the inhalation of carbon dioxide gas for the user 34.

In addition, the oxygen content in the body of the user 34 is able to be measured and calculated. Based on the oxygen content, the preset ratio of carbon dioxide gas to high pressure oxygen is able to be further controlled as follows. The calculation method comprises steps of:

obtaining the first linear relationship between oxygen saturation and the dual wavelength light absorption ratio based on optical absorption measurement method and optical pulse plethysmography, wherein the first linear relationship further comprises a linear relationship between oxygen saturation and body mass indexes of the subject to be detected;

obtaining the second linear relationship between oxygen saturation and the intensity of incident light and detected light passing through the body surface based on the first spectrum signature and the second spectrum signature as well as the intensity of incident light and the detected light passing through the body surface of red light and infrared light;

forming a multiple linear regression model by combining the first linear relationship with the second linear relationship; and calculating the oxygen saturation based on the multiple linear regression model.

The formula of the first linear relationship is as follows:

$$S_aO_2 = \frac{\varepsilon_{r1}}{\varepsilon_{r1} - \varepsilon_{o1}} - \frac{\varepsilon_{r2}(\varepsilon_{o1} C_{Hb}O_2 + \varepsilon_{r1} C_{Hb})}{(\varepsilon_{r1} - \varepsilon_{o1})(\varepsilon_{o2} C_{Hb}O_2 + \varepsilon_{r2} C_{Hb})} - \alpha\frac{W}{H^2},$$

$$K = \frac{\varepsilon_{o1} C_{Hb}O_2 + \varepsilon_{r1} C_{Hb}}{\varepsilon_{o2} C_{Hb}O_2 + \varepsilon_{r2} C_{Hb}},$$

wherein $S_aO_2$ is oxygen saturation, K is dual wavelength light absorption ratio, $\varepsilon_{o1}$ is oxygenated hemoglobin light absorption coefficient under red light, $\varepsilon_{o2}$ is oxygenated hemoglobin light absorption coefficient under infrared light, $\varepsilon_{r1}$ is reduced hemoglobin light absorption coefficient under red light, $\varepsilon_{r2}$ is reduced hemoglobin light absorption coefficient under infrared light, $C_{Hb}O_2$ is oxygenated hemoglobin light content, $C_{Hb}$ is reduced hemoglobin content, a is empirical coefficient and ranges from 0.1 to 0.3, W is the weight of the object to be detected (unit: Kg); H is the height of the object to be detected (unit: m).

The formula of the second linear relationship is as follows:

$$S_aO_2 = 1 - \frac{A\varepsilon_{o2} - \varepsilon_{o1}}{A\varepsilon_{r2} - \varepsilon_{r1} + \varepsilon_{o1} - A\varepsilon_{o2}},$$

$$A = \left(\ln\frac{I_{01}}{I_{test1}}\right) / \left(\ln\frac{I_{02}}{I_{test2}}\right),$$

wherein $S_aO_2$ is oxygen saturation, A is ratio of red light absorption to infrared light absorption, $\varepsilon_{o1}$ is oxygenated hemoglobin light absorption coefficient under red light, $\varepsilon_{o2}$ is oxygenated hemoglobin light absorption coefficient under infrared light, $\varepsilon_{r1}$ is reduced hemoglobin light absorption coefficient under red light, $\varepsilon_{r2}$ is reduced hemoglobin light absorption coefficient under infrared light, $I_{01}$ is the intensity of red light incident light, $I_{02}$ is the intensity of infrared light incident light, $I_{test1}$ is the intensity of light detected after red light passes through the body surface; $I_{test2}$ is the intensity of light detected after infrared light passes through the body surface.

The formula of the formed multiple linear regression model is as follows:

$$Y(S_aO_2) = \beta_0 + \beta_1\left[\frac{\varepsilon_{r1}}{\varepsilon_{r1} - \varepsilon_{o1}} - \frac{\varepsilon_{r2}(\varepsilon_{o2} C_{Hb}O_2 + \varepsilon_{r1} C_{Hb})}{(\varepsilon_{r1} - \varepsilon_{o1})(\varepsilon_{o2} C_{Hb}O_2 + \varepsilon_{r2} C_{Hb})} - \alpha\frac{W}{H^2}\right] + \beta_2\left[1 - \frac{A\varepsilon_{o2} - \varepsilon_{o1}}{A\varepsilon_{r2} - \varepsilon_{r1} + \varepsilon_{o1} - A\varepsilon_{o2}}\right]$$

wherein $Y(S_aO_2)$ is oxygen saturation determined based on the multiple linear regression model, and $\beta_0$, $\beta_1$ and $\beta_2$ are the regression coefficients of the multiple linear regression model.

Obviously, those skilled in the art may make various alterations and variants of the present invention without deviating from the spirit and scope of the present invention. Thus, if these modifications and variations of the present invention fall within the scope of the claims of the present invention and their equivalents, the present invention is also intended to include these modifications and variations.

What is claimed is:

1. A breathing device with carbon dioxide compensation function, which comprises:

a ventilator (1), wherein an air source pipeline, a low pressure oxygen source pipeline, a high pressure oxygen source pipeline, a carbon dioxide source pipeline, and a gas supply pipeline are set in the ventilator (1); and a breathing pipeline which is set outside the ventilator (1), wherein:

air from an air source (2) enters the ventilator (1) through the air source pipeline, low pressure oxygen from a low pressure oxygen source (3) is mixed with the air in the air source pipeline through the low pressure oxygen source pipeline; mixed breathing gas enters the gas supply pipeline which is located behind a third check valve (218), is transmitted outside the ventilator (1) through the gas supply pipeline, and is configured to be inhaled by a user (34) through the breathing pipeline;

high pressure oxygen from a high pressure oxygen source (4) enters the ventilator (1) through the high pressure oxygen source pipeline, carbon dioxide gas from a carbon dioxide source (5) and the high pressure oxygen in the high pressure oxygen source pipeline are mixed through the carbon dioxide source pipeline and form therapeutic gas; the therapeutic gas enters the gas supply pipeline, is transmitted outside the ventilator (1) through the gas supply pipeline, and is configured to be inhaled by the user (4) through the breathing pipeline for treatment, wherein the carbon dioxide gas is mixed with the high pressure oxygen in a preset ratio, so as to adjust a content of carbon dioxide in a body of the user (34);

wherein a first filter (207) is provided on the air source pipeline, a second filter (307) and a first check valve (108) are provided on the low pressure oxygen source pipeline, the low pressure oxygen flows through the second filter (307) and first check valve (108) in sequence and enters an oxygen flow sensor (10), the low pressure oxygen and the air from the oxygen flow sensor (10) enter a breathing gas generator (11) through a second check valve (208), and are mixed by the breathing gas generator (11) for forming breathing gas;

a first pressure sensor (9) is provided on the low pressure oxygen source pipeline and is located between the first check valve (108) and the oxygen flow sensor (10) for measuring a pressure of the low pressure oxygen in the low pressure oxygen source pipeline, the breathing gas enters the gas supply pipeline through the third check valve (218);

wherein a third filter (413), a first flow control valve (14), and a directional valve (15) are provided on the high pressure oxygen source pipeline, a second pressure sensor (24) is located between the third filter (413) and the first flow control valve (14); when the directional valve (15) is opened positively, the high pressure oxygen enters the gas supply pipeline through the third filter (413), the first flow control valve (14), and the directional valve (15) on the high pressure oxygen source pipeline;

a fourth filter (513), a third pressure sensor (25) and a second flow control valve (16) are provided on the carbon dioxide source pipeline in sequence, the carbon dioxide gas and the high pressure oxygen are mixed through the fourth filter (513), the third pressure sensor (25) and the second flow control valve (16) on the carbon dioxide source pipeline and form therapeutic gas, the therapeutic gas enters the gas supply pipeline;

the third pressure sensor (25) measures a pressure of the carbon dioxide gas in the carbon dioxide source pipeline; a ratio of oxygen to the carbon dioxide gas in the therapeutic gas is adjusted through adjusting a flow of the high pressure oxygen and the carbon dioxide gas by the first flow control valve (14) and the second flow control valve (16), so as to allow the ratio reaches the preset ratio.

2. The breathing device with carbon dioxide compensation function according to claim 1, wherein an oxygen sensor (27), a carbon dioxide sensor (12), a fourth pressure sensor (35) and a gas flow sensor (28) are provided on the gas supply pipeline;

the oxygen sensor (27) detects an oxygen concentration in the gas supply pipeline, the carbon dioxide sensor (12) detects a carbon dioxide concentration in the gas supply pipeline, the fourth pressure sensor (35) detects a gas pressure in the gas supply pipeline, and the gas flow sensor (28) detects a gas flow in the gas supply pipeline.

3. The breathing device with carbon dioxide compensation function according to claim 2, wherein a humidifier (29) and a nebulizer (32) are provided on the breathing pipeline, a fifth pressure sensor (30) is located between the humidifier (29) and the nebulizer (32), the breathing gas or the therapeutic gas is configured to enter a body of the user (34) through the nebulizer (32);

atomizing gas of the nebulizer (32) is from the high pressure oxygen in the high pressure oxygen source pipeline, the high pressure oxygen enters an atomizing pipeline through a shut-off valve (19), and then enters the nebulizer (32) through a first throttle valve (21) for atomizing medication.

4. The breathing device with carbon dioxide compensation function according to claim 3, wherein the breathing gas or the therapeutic gas is configured to enter the body of the user (34) through the nebulizer (32) comprises:

the breathing gas or the therapeutic gas is configured to enter the body of the user (34) through the nebulizer (32) via a mask (33) or a respiratory tube;

when the user (34) exhales gas through the mask (33) or the respiratory tube, the exhaled gas enters an expiratory pipeline, the expiratory pipeline is provided with a diaphragm regulating valve (31), and the exhaled gas enters an external environment (23) through the diaphragm regulating valve (31);

the high pressure oxygen source pipeline is connected with a PEEP (positive end-expiratory pressure) regulating pipeline, the PEEP regulating pipeline is provided with a pressure regulating valve, a sixth pressure sensor (20) and a second throttle valve (22); the sixth pressure sensor (20) is connected with the diaphragm regulating valve (31) for detecting PEEP; a pressure of the diaphragm regulating valve (31) is adjusted by the sixth pressure sensor (20) and the second throttle valve;

the pressure regulating valve is opened to a position according to a preset PEEP value, and diverted high pressure oxygen in the high pressure source pipeline enters the external environment through the second throttle valve.

5. The breathing device with carbon dioxide compensation function according to claim 3, wherein the fifth pressure sensor (30) is connected with an alarm; when the fifth pressure sensor (30) detects that a pressure exceeds a preset range, an alarm instruction is sent to the alarm, and the alarm sends out an abnormal pressure alarm to remind occurrence of gas path blockage or gas leakage.

6. The breathing device with carbon dioxide compensation function according to claim 1, wherein when the directional valve (15) is opened reversely, the high pressure oxygen in the high pressure oxygen source pipeline will enter the gas supply pipeline from a front end of the second check valve (208) instead of a rear end of the third check valve (218).

7. The breathing device with carbon dioxide compensation function according to claim 1, wherein the breathing device further comprises an auxiliary gas source pipeline, the auxiliary gas source pipeline is provided with a fifth filter (613) and a third flow control valve (17), and a seventh pressure sensor (26) is located between the fifth filter (613) and the third flow control valve (17);

auxiliary gas from an auxiliary gas source (6) is mixed with the high pressure oxygen and the carbon dioxide gas through the auxiliary gas source pipeline, and mixed gas enters the gas supply pipeline;

the auxiliary gas from the auxiliary gas source (6) comprises carbon dioxide and medical gas used by a medical industry for inhalation by the user (34).

* * * * *